United States Patent [19]

Ditrich

[11] Patent Number: 5,489,731
[45] Date of Patent: Feb. 6, 1996

[54] PREPARATION OF AROMATIC VINYL COMPOUNDS

[75] Inventor: Klaus Ditrich, Bad Duerkheim, Germany

[73] Assignee: BASF Aktiengesellschaft, Ludwigshafen, Germany

[21] Appl. No.: 158,775

[22] Filed: Dec. 1, 1993

[30] Foreign Application Priority Data

Dec. 1, 1992 [DE] Germany .................. 94 240 321.9

[51] Int. Cl.$^6$ .................. C07C 1/20; C07C 1/207; C07C 2/00
[52] U.S. Cl. .................. 585/437; 585/435; 585/436
[58] Field of Search .................. 585/435, 436, 585/437

[56] References Cited

FOREIGN PATENT DOCUMENTS

| 2936237 | 3/1981 | Germany . |
| 388300 | 3/1959 | Switzerland . |
| 812522 | 4/1959 | United Kingdom . |

OTHER PUBLICATIONS

Reimann et al.: Synthese von cis-a,11,a-Dimethyl-4,5,6,6a,7a,8,9,10,11a-decahydro-7H-naphtho (1-8 fg) isochinoliner Arch. Pharmacol., vol. 322, 1989, pp. 159-164.

Arch. Pharm 322 (1989) 159.
Synth. Commun. 6 (1976) 53.
Chem. Abst., vol. 108, No. 15, Apr. 11, 1988, abstract no. 132118c.

*Primary Examiner*—Ponnathapura Achutamurthy
*Attorney, Agent, or Firm*—Keil & Weinkauf

[57] ABSTRACT

Aromatic vinyl compounds of the formula I $$Ar-CH=CHR \qquad I$$

where Ar is an aromatic radical, and R is hydrogen, $C_1$–$C_4$-alkyl or unsubstituted or substituted phenyl, are prepared by reacting an alcohol of the formula II $$Ar-CH_2OH \qquad II$$

or an ester of the formula III $$Ar-CH_2O-\underset{\underset{\|}{O}}{C}R' \qquad III$$

where R' is hydrogen or $C_1$–$C_4$-alkyl, in aqueous solution with a triarylphosphine and a strong acid and then, in the presence of a mineral base, with an aldehyde of the formula IV $$R-CHO \qquad IV.$$

3 Claims, No Drawings

PREPARATION OF AROMATIC VINYL COMPOUNDS

The present invention relates to a novel process for preparing aromatic vinyl compounds of the formula I $$Ar-CH=CHR \qquad \text{I}$$

where Ar is an aromatic radical, and R is hydrogen, $C_1$–$C_4$-alkyl or unsubstituted or substituted phenyl.

Arch. Pharm. 322 (1989) 159 discloses the reaction of a 1-tetralol with triphenylphosphonium bromide in benzene to give the corresponding tetralyltriphenylphosphonium bromide. Triphenylphosphoniumbromide is prepared in a separate reaction for this purpose.

Synth. Commun. 6 (1976) 53 describes the preparation of some p-substituted styrene derivatives. Parasubstituted benzyl halides are reacted with triphenylphosphine in chloroform to prepare benzylphosphonium salts, which are isolated and then reacted with aqueous formalin solution and sodium hydroxide to give the corresponding styrene derivatives.

It is an object of the present invention to provide a process for preparing aromatic vinyl compounds which avoids the isolation of intermediates.

We have found that this object is achieved by a process for preparing aromatic vinyl compounds of the formula I $$Ar-CH=CHR \qquad \text{I}$$

where Ar is an aromatic radical, and R is hydrogen, $C_1$–$C_4$-alkyl or unsubstituted or substituted phenyl, which comprises reacting an alcohol of the formula II $$Ar-CH_2OH \qquad \text{II}$$

or an ester of the formula III $$Ar-CH_2O-\overset{O}{\underset{\|}{C}}R' \qquad \text{III}$$

where R' is hydrogen or $C_1$–$C_4$-alkyl, in aqueous solution with a triarylphosphine and a strong acid and then, in the presence of a mineral base, with an aldehyde of the formula IV $$R-CHO \qquad \text{IV}$$

where R is hydrogen, $C_1$–$C_4$-alkyl or unsubstituted or substituted phenyl.

The following equation outlines the reaction of a benzyl alcohol:

$$Ar-CH_2OH \xrightarrow[\text{2. RCHO/MOH}]{\text{1. HX/PR''}_3} Ar-CH=CHR$$
$$\text{II} \qquad\qquad\qquad\qquad \text{I}$$
$$+P(O)R'_3 + MX + H_2O$$

X=anion of acid
R''=aryl
M=alkali metal

The alcohols II and the esters III are known or can be prepared by known methods. They comprise, inter alia, benzyl alcohols or their esters which may have one or more substituents on the aromatic ring. Suitable and preferred substituents are $C_1$–$C_4$-alkoxy such as methoxy, ethoxy, isopropoxy and n-propoxy, $C_1$–$C_4$-alkylthio such as methylthio, ethylthio and n-propylthio, $C_1$–$C_6$-alkyl such as methyl, ethyl, isopropyl and n-propyl, $C_2$–$C_6$-alkenyl such as vinyl, $C_2$–$C_6$-alkynyl, carboxyl, nitro, cyano, hydroxyl, halogen such as fluorine, chlorine, bromine and iodine, and halo-$C_1$–$C_4$-alkyl such as trifluoromethyl. If other benzylic hydroxyl groups or ester moieties are present, the reaction can also take place more than once. Mention should also be made of naphthalene- and anthracenemethanols, which may also be substituted.

The alcohols II and the esters III are reacted with triarylphosphines which may have substituents on the aromatic radicals, but triphenylphosphine is preferred.

The alcohol II or the ester III and the phosphine are reacted with strong acids. The acids normally have a $pK_a$ below zero. Examples are mineral acids such as hydrochloric acid, hydrobromic acid and sulfuric acid, carboxylic acids such as acetic acid and trifluoroacetic acid, and sulfonic acids such as p-toluenesulfonic acid. Nitric acid should not be used because it may lead to uncontrollable explosive reactions.

As a rule, the phosphine is used in a small excess of from 1:1 to 3:1 relative to the alcohol II or the ester III. The acid is generally employed in a larger excess, i.e. about 1.5 to 20 equivalents of acid per equivalent of alcohol.

The reaction can be carried out by mixing the starting material, the phosphine and the acid in aqueous solution and heating at from 50° to 100° C. for from 1 to 3 hours to increase the rate.

For the subsequent reaction, an aldehyde IV O=CH—R where R is hydrogen, $C_1$–$C_4$-alkyl or unsubstituted or substituted phenyl, such as alkylphenyl, is added to the resulting solution. The aldehyde is preferably formaldehyde, but other suitable examples are acetaldehyde, n-propionaldehyde and benzaldehyde.

The aldehyde is preferably used in the form of a mixture with water which usually contains from 20 to 40% by weight of aldehyde. The molar ratio of aldehyde IV to alcohol II or ester III is usually from 1:1 to 50:1, preferably from 3:1 to 15:1.

A mineral base is also added. Alkaline earth metal hydroxides such as calcium hydroxide and barium hydroxide are just as suitable as alkali metal hydroxides such as lithium hydroxide or, preferably sodium hydroxide and potassium hydroxide. The bases are usually employed as 20–60% strength aqueous solutions.

The reaction can be carried out at from 0° to 100° C., preferably 20°–70° C. It is generally complete after 15 hours, but 3 hours are often sufficient. The reaction can be carried out under elevated pressure of up to about 10 bar, but it is usually carried out under atmospheric pressure.

The products are isolated by conventional methods, for example by filtering off the triarylphosphine oxide, extracting with an organic solvent and crystallizing or distilling.

It may also be advantageous for certain products to carry out the reaction in the presence of an organic solvent such as dichloromethane, in which case the products are extracted directly into the organic phase. In this variant it is also possible to use phase-transfer catalysts such as quaternary ammonium compounds, e.g. triethylbenzylammonium chloride.

The process according to the invention allows aromatic vinyl compounds to be prepared from alcohols II or esters III in an easily carried out one-pot reaction in aqueous solution. The isolation of phosphonium salts is unnecessary. In addition, the triarylphosphine oxide formed in the reaction can easily be removed.

The products are used for preparing polymers. For example, p-hydroxystyrene can be prepared and, as polymer, be used as binder for photoresists (ACS Symp. Ser. 412 (1989)).

EXAMPLES

General method for Examples 1–8

1.5 mol of 37% strength aqueous acid were added to a mixture of 1 mol of alcohol II and 1.05 mol of triphenylphosphine. The mixture was heated at 85° C. for 2 hours, and 500 ml (6.6 mol) of 37% strength aqueous formaldehyde solution and 425 ml (8.0 mol) of 50% strength sodium hydroxide solution were added. The solution was maintained at 60° C. for 3 hours. After filtration, the product was isolated by extraction with n-hexane and was distilled.

| Example | Substituents on the benzyl alcohol | Acid | Yield [%] |
|---|---|---|---|
| 1 | 4-OCH₃ | HBr | 95 |
| 2 | 2-I | HBr | 70 |
| 3 | 3-Cl, 4-Cl | HBr | 94 |
| 4 | 4-Cl | HCl | 100 |
| 5 | 3-OMe, 4-OMe | HBr | 40 |
| 6 | 3-OMe, 4-OMe, 5-OMe | HBr | 75 |
| 7 | 2-OMe, 3-OMe | HBr | 86 |
| 8 | 4-COOH | HCl | 68 |

EXAMPLES 9–14

1 mol of benzyl ester III was reacted as in Examples 1–8.

In Example 14, the amounts of the reagents for 1 mol of benzyl ester were doubled because a double reaction to form 1,4-divinylbenzene takes place.

| Example | Substituents on the aromatic radical | R' | Acid | Yield [%] |
|---|---|---|---|---|
| 9 | 4-CH₃ | H | HCl | 99 |
| 10 | 4-CH₃ | CH₃ | HCl | 96 |
| 11 | 2-CH₃ | CH₃ | HCl | 93 |
| 12 | 3-CH₃ | CH₃ | HCl | 87 |
| 13 | 4-F | CH₃ | HBr | 29 |
| 14 | 4-(CH₂OCOCH₃) | CH₃ | HCl | 74 |

EXAMPLES 15–17

1.5 tool of 37% strength aqueous acid were added to a mixture of 1 mol of alcohol II and 1.05 mol of triphenylphosphine. The mixture was heated at 85° C. for 2 h, and 5.0 mol of aldehyde IV in 1 l of dichloromethane were added. 6 mol of sodium hydroxide in the form of a 50% strength aqueous solution were added and then the mixture was stirred at room temperature for 14 h, extracted with dichloromethane and worked up by chromatography.

| Example | Substituents on the benzyl alcohol | R | Acid | Yield [%] |
|---|---|---|---|---|
| 15 | 4-OCH₃ | Phenyl | HCl | 50 |
| 16 | 4-OCH₃ | CH₃ | HCl | 52 |
| 17 | 4-OCH₃ | 1-methylethyl | HCl | 35 |

We claim:
1. A two-step process for preparing aromatic vinyl compounds of the formula I

$$Ar-CH=CHR \qquad \qquad I$$

where Ar is an aromatic radical, and R is hydrogen, $C_1$–$C_4$-alkyl or unsubstituted or substituted phenyl, which process comprises 1) reacting an alcohol of the formula II $$Ar-CH_2OH \qquad \qquad II$$

or an ester of the formula III $$Ar-CH_2O-\overset{\overset{\displaystyle O}{\|}}{C}R' \qquad \qquad III$$

where R' is hydrogen or $C_1$–$C_4$-alkyl, in aqueous media with a triarylphosphine and a strong acid and 2) subsequently, adding in the presence of an alkaline earth or alkali metal hydroxide, an aldehyde of the formula IV $$R-CHO \qquad \qquad IV$$

where R is hydrogen, $C_1$–$C_4$-alkyl or unsubstituted or substituted phenyl, to the reaction product of step 1, to form the compound of the formula I.

2. A process as claimed in claim 1, wherein the triarylphosphine is triphenylphosphine.

3. A process as claimed in claim 1, wherein p-methoxybenzyl alcohol is used as the alcohol of formula II, and formaldehyde is used as aldehyde.

* * * * *